United States Patent [19]

De Lacharriere et al.

[11] Patent Number: 5,993,833
[45] Date of Patent: *Nov. 30, 1999

[54] HISTAMINE ANTAGONIST, AN INTERLEUKIN-1 ANTAGONIST AND/OR A TNF ALPHA ANTAGONIST IN A COSMETIC, PHARMACEUTICAL OR DERMATOLOGICAL COMPOSITION

[75] Inventors: Olivier De Lacharriere, Paris; Lionel Breton, Versailles; Catherine Cohen, Paris, all of France

[73] Assignee: Societe L'Oreal S.A., Paris, France

[ * ] Notice: This patent is subject to a terminal disclaimer.

[21] Appl. No.: 08/879,889

[22] Filed: Jun. 20, 1997

Related U.S. Application Data

[62] Division of application No. 08/580,291, Dec. 28, 1995, Pat. No. 5,658,581.

[30] Foreign Application Priority Data

Dec. 28, 1994 [FR] France .................................. 94 15796

[51] Int. Cl.$^6$ ...................................................... A61K 7/48
[52] U.S. Cl. ........................... 424/401; 424/70.1; 514/25; 514/263; 514/339; 514/352; 514/382; 514/840; 514/859; 514/937; 514/944
[58] Field of Search ................................... 424/401, 70.1; 514/840, 859, 937, 944, 25, 263, 339, 352, 382

[56] References Cited

U.S. PATENT DOCUMENTS 5,002,941  3/1991  Adams et al. .......................... 514/186
5,658,581  8/1997  De Lacharriere et al. ............. 424/401

*Primary Examiner*—Jyothsna Venkat
*Attorney, Agent, or Firm*—Burns, Doane, Swecker & Mathis, L.L.P.

[57] ABSTRACT

The invention relates to the use of a histamine antagonist, an interleukin-1-antagonist and/or a TNF antagonist in a cosmetic, pharmaceutical or dermatological composition for treating sensitive skins. It relates especially to the use of a histamine antagonist, an interleukin-1 antagonist and/or a TNF alpha antagonist for preventing and/or combating skin irritations and/or sores and/or erythema and/or dysaesthetic sensations and/or sensations of inflammation and/or pruritus and/or prickling and/or tingling and/or discomfort and/or tightness of the skin and/or mucosae. It also relates to a composition containing a histamine antagonist, an interleukin-1 antagonist and/or a TNF alpha antagonist which limits or eliminates the irritant side-effects of certain products, and in particular of certain cosmetic, dermatological or pharmaceutical active agents.

20 Claims, No Drawings

HISTAMINE ANTAGONIST, AN INTERLEUKIN-1 ANTAGONIST AND/OR A TNF ALPHA ANTAGONIST IN A COSMETIC, PHARMACEUTICAL OR DERMATOLOGICAL COMPOSITION

This application is a divisional of application Ser. No. 08/580,291, filed Dec. 28, 1995 now an U.S. Pat. No. 5,658,581.

The present invention relates to the use of a histamine antagonist, an interleukin-1 antagonist and/or TNF alpha antagonist in a cosmetic, pharmaceutical or dermatological composition for topical application, intended, in particular, for the treatment of sensitive skins, as well as to a composition containing a histamine antagonist, an interleukin-1 antagonist and/or a TNF alpha antagonist for the purpose of decreasing or even abolishing the irritant effects of certain products, and in particular of certain active agents used in the cosmetics, pharmaceutical or dermatological field.

It is known that some skins are more sensitive than others. The symptoms of sensitive skin were hitherto poorly characterized and the problem of these skins was, as a result, poorly defined; nobody understood precisely the process involved in sensitivity—non-allergic cutaneous hyperreactivity—of the skin. Some workers believed that a sensitive skin was a skin which reacted to cosmetic products, others that such a skin was one which reacted to several external factors, not necessarily associated with cosmetic products.

Some tests have been tried in an effort to pinpoint sensitive skins, for example tests involving lactic acid and DMSO, which are known to be irritant substances: see, for example, the paper by K. Lammintausta et al., Dermatoses, 1988, 36, pages 45–49; and the paper by T. Agner and J. Serup, Clinical and Experimental Dermatology, 1989, 14, pages 214–217. However, these tests did not enable sensitive skins to be characterized completely.

Moreover, sensitive skins were likened to allergic skins.

Since the characteristics of sensitive skins were poorly understood, it was very difficult to treat them hitherto, and they were treated indirectly, for example by limiting the use of products having an irritant character, such as surfactants, preservatives or perfumes as well as certain active agents, in cosmetic or dermatological compositions.

The Applicant has carried out numerous clinical tests and has been able to determine the symptoms associated with sensitive skins. These symptoms are, in particular, subjective signs which are essentially dysaesthetic sensations. Dysaesthetic sensations are understood to mean more or less painful sensations experienced in an area of the skin, such as prickling, tingling, itching or pruritus, burning, inflammation, discomfort, tightness, and the like.

The Applicant was able to show, in addition, that a sensitive skin was not an allergic skin. In effect, an allergic skin is a skin which reacts to an external agent, an allergen, which triggers an allergic reaction. This is an immunological process which takes place only when an allergen is present and which affects only sensitized subjects. The essential characteristic of sensitive skin is, according to the Applicant, on the contrary, a mechanism of response to external factors, which can affect any individual, even if individuals with so-called sensitive skin react to them more quickly than do others. This mechanism is not immunological.

The Applicant has now found that sensitive skins could be divided into two major clinical forms, irritable skins and intolerant skins.

An irritable skin is a skin which reacts by pruritus, that is to say by itching or by prickling, to different factors such as the environment, emotions, foods, windy conditions, rubbing, shaving soap, surfactants, hard water with a high chalk concentration, temperature changes or wool. In general, these signs are associated with a dry skin with or without sores, or with a skin which displays erythema.

An intolerant skin is a skin which reacts by sensations of inflammation or of tightness, by pruritus, that is to say by itching or prickling, by tingling and/or red blotches, to different factors such as the environment, emotions and foods. In general, these signs are associated with erythema and with a skin with or without sores.

"Sensitive" scalps have a more unequivocal symptomatology: the sensations of pruritus and/or of prickling and/or inflammation are essentially triggered by local factors such as rubbing, soap, surfactants, hard water with a high chalk concentration, shampoos or lotions. These sensations are also sometimes triggered by factors such as the environment, emotions and/or foods. Erythema and hyperseborrhoea of the scalp as well as a dandruff state are frequency associated with the above signs.

Moreover, in some anatomical regions, such as the major folds (inguinal, genital, axillary, popliteal, anal and inframammary regions, bend of the elbow) and the feet, sensitive skin manifests itself in pruriginous sensations and/or dysaesthetic sensations (inflammation, prickling) associated especially with sweating, with rubbing, with wool, with surfactants, with hard water with a high chalk concentration and/or with temperature changes.

To determine whether a skin is sensitive or otherwise, the Applicant has also developed a test. In effect, after performing a large number of tests with the object of defining a sensitive skin, it found, surprisingly, that there was a link between persons having sensitive skin and those who reacted to a topical application of capsaicin.

The capsaicin test consists in applying 0.05 ml of a cream containing 0.075% of capsaicin to approximately 4 $cm^2$ of skin, and noting the appearance of subjective signs caused by this application, such as prickling, burning and itching. In subjects having sensitive skins, these signs appear between 3 and 20 minutes after the application, and are followed by the appearance of an erythema which begins at the periphery of the area of application.

Hitherto, capsaicin was used as a medicinal product, especially for treating the pains of shingles. Capsaicin causes a release of neuropeptides, and especially of tachykinins which originate from nerve endings of the epidermis and the dermis. The Applicant found that the physiopathological mechanism common to all the states of sensitive skins was associated with a great capacity to release tachykinins and more especially substance P in the skin. It is known, in addition, that substance P released by epidermal sensory endings induces a cascade of biochemical events in which the first steps affect the mast cells. The binding of substance P to mast cell receptors induces a release of numerous pro-inflammatory mediators, among them histamine, serotonin, interleukin-1 (IL-1), interleukin-6 (IL-6), interleukin-8 (IL8) and tumour necrosis factor alpha (TNF alpha).

Moreover, the Applicant found that sensitive skins as are defined above are, in addition, characterized by high levels of interleukin-1 and/or of histamine in the superficial layers of the epidermis. These levels rise proportionately as the state of reactivity of the skin increases.

The Applicant has now discovered that the essential characteristics of sensitive skins (irritation reactions and cutaneous intolerance reactions) are associated with the release of substance P and consequently with the release of histamine, of interleukin-1 and particularly of TNF alpha, and that interleukin-1 antagonists and/or TNF alpha antagonists and/or histamine antagonists may be used in the preventive and/or curative treatment of sensitive skins.

Histamine, interleukin-1 and/or TNF alpha "antagonists" are understood to mean all substances capable of inhibiting the release and/or synthesis and/or receptor binding of histamine, of interleukin-1 and/or of TNF alpha, respectively. The antagonists inhibiting the receptor binding of histamine are agents specific for the type 1 histamine ($H_1$) receptor.

In addition, the Applicant found that the addition of interleukin-1 antagonists and/or of TNF alpha antagonists to cosmetic, pharmaceutical or dermatological compositions for topical application containing irritant products (alpha-hydroxy acids, retinoids, benzoyl peroxide, etc.) also enabled the irritation reactions usually caused by these products to be decreased or even eliminated. These irritation reactions manifest themselves within moments following application, in dysaesthetic sensations (inflammation, burning, itching or pruritus sensations, prickling sensations, tightness, etc.), and/or in red blotches, and/or in oedema. These irritation states may also manifest themselves some time after application, in the persistence, appearance or reappearance of the abovementioned dysaesthetic sensations and/or in red blotches and/or scales; these skin irritation states may assume the appearance of plaques of cutaneous xerosis and/or sores.

Moreover, histamine release induced by neurogenic inflammation causes a vasodilatation which manifests itself in erythema, oedema and pruritus. Thus, the addition of histamine antagonists specific for the $H_1$ receptors to irritant cosmetic, pharmaceutical or dermatological compositions also enables the irritation reactions usually caused by these products to be decreased or even eliminated.

To treat sensitive skins, the Applicant hence envisaged the use of histamine antagonists, interleukin-1 antagonists and/or TNF alpha antagonists. It found, in effect, surprisingly, that the incorporation of histamine antagonists, interleukin-1 antagonists and/or TNF alpha antagonists in a cosmetic, pharmaceutical or dermatological composition enables the irritation and/or dysaesthetic sensations and/or pruritus of the skin and/or mucosae to be avoided.

Hence the subject of the present invention is the use of at least one compound chosen from interleukin-1 antagonists, TNF alpha antagonists and combinations thereof, in a composition containing a cosmetically, pharmaceutically or dermatologically acceptable medium, for treating sensitive skins.

The subject of the present invention is also the use in a topical composition of at least one compound chosen from interleukin-1 antagonists, TNF alpha antagonists and combinations thereof, for preventing and/or combating skin irritations and/or sores and/or erythema and/or sensations of inflammation and/or of dysaesthesia and/or pruritus and/or prickling and/or tingling and/or discomfort and/or tightness of the skin and/or mucosae.

According to the invention, the topical composition may contain, in addition, a constituent chosen from histamine antagonists and combinations thereof.

The subject of the present invention is also the use in a topical composition of at least one constituent chosen from histamine antagonists and combinations thereof, for preventing and/or combating skin irritations and/or sores and/or sensations of inflammation and/or of dysaesthesia and/or prickling and/or tingling and/or discomfort and/or tightness of the skin and/or mucosae.

A cosmetically, dermatologically or pharmaceutically acceptable medium is a medium which is compatible with the skin, scalp, nails and mucosae. The composition containing a histamine antagonist and/or an interleukin-1 antagonist and/or a TNF alpha antagonist may hence be applied to the face, neck, hair and nails, or any other area of the skin of the body such as the major folds (axillary or inframammary regions, bend of the elbow and the like).

For a substance to be recognized as a histamine, interleukin-1 (IL-1) or TNF alpha receptor antagonist, it must satisfy, in particular, the following characteristic:

have a histamine, IL-1 or TNF alpha receptor antagonist pharmacological activity, that is to say induce a coherent pharmacological response in at least one of the following tests:
for histamine receptor antagonists: an inhibition of the contraction of smooth muscles induced by the administration of histamine;
for IL-1 receptor antagonists: inhibition of the IL-1 induced adhesion of macrophages to endothelial cells, or inhibition of the IL-1-induced release of superoxide anions from neutrophils;
for TNF alpha receptor antagonists: inhibition of the TNF alpha-induced adhesion of macrophages to endothelial cells, or inhibition of the TNF alpha-induced release of superoxide anions from neutrophils or inhibition of the mitogenic activity of TNF alpha with respect to the fibroblasts of the dermis.

The histamine, interleukin-1 (IL-1) or TNF alpha antagonist may, in addition, have a selective affinity for the specific receptors for these compounds: $H_1$, IL-1 and TNF alpha.

For a substance to be recognized as an antagonist of the release and/or synthesis of histamine, of interleukin-1 or of TNF alpha, it must satisfy, in particular, the following characteristic:

inhibition of histamine release by mast cells stimulated with the compound 48/80 or stimulated with a calcium ionophore (A23 187)

inhibition of the release of interleukin-1 or of TNF alpha by monocytes (U937 cells) differentiated with a phorbol ester (PMA).

Hiterto, histamine antagonists were used to treat allergic disorders systemically. Interleukin-1 antagonists are currently being tested in certain chronic inflammatory disorders such as rheumatic disorders, septic shock, asthma, psoriasis and ocular allergies. TNF alpha antagonists are currently being tested for treating fever, septic shock and cachexia.

The antagonists of the invention are, in particular, compounds comprising at least one heterocycle and nitrogen compounds comprising at least one benzene ring.

The histamine $H_1$ receptor antagonists which can be used in the invention are those traditionally used in the treatment of allergic and anaphylactic states, as well as those for combating travel sickness. These compounds can be, for example, diethylenediamine derivatives such as cinnarizine, cyclizine; aminopropane derivatives such as dexchloropheniramine, triprolidine; phenothiazine derivatives such as promethazine, alimemazine; and also the compounds mentioned on pages 116 to 118 of the book by Joseph R. Prous, The Year's Drug News, Therapeutic Targets, 1994 edition, Prous Science Publishers, such as cetirizine HCl, ebastine, loratadine, setastine HCl.

The histamine release inhibitors are, in particular, oxygen- or sulphur-containing heterocyclic compounds such as furan derivatives, benzofuran derivatives, thiophene derivatives and benzothiophene derivatives, optionally containing nitrogenous substituents, such as those described in the documents U.S. Pat. No. 4,931,459, U.S. Pat. No. 4,910,317 and EP-A-299,457, and more especially alkoxy- and/or aryloxytetrazolylbenzofurancarboxamides or alkoxy- and/or aryloxytetrazolylbenzothiophenecarboxamides. By way of example, 5-methoxy-3-phenoxy-N-(1H-tetrazol-5-yl)benzothiophene-2-carboxamide, 5-methoxy-3-(1-methylethoxy)-N-(1H-tetrazol-5-yl)benzothiophene-2-carboxamide, 6-methoxy-3-(1-methylethoxy)-N-(1H-tetrazol-5-yl)benzothiophene-2-carboxamide, 5-methoxy-3-(1-methylethyl)-N-(1H-tetrazol-5-yl)benzothiophene-2-carboxamide, 3-benzyloxy-5-methoxy-N-(1H-tetrazol-5-yl) benzothiophene-2-carboxamide and 5-methoxy-3-phenoxy-N-(1H-tetrazol-5-yl)benzothiophene-2-carboxamide may be mentioned.

An interleukin-1 release antagonist which can be used in the invention can be auranofin or SKF-105809. (6,7-dihydro-2-[4-(methylsulfinyl)phenyl]-3-)4-pyridinyl)-5Hh-pyrrolo[1,2-a]imidazole. An interleukin-1 synthesis antagonist can be lactoferin.

The TNF alpha receptor antagonists and the inhibitors of TNF alpha release and/or synthesis which can be used in the invention are, in particular, lisophyline, A802715, A-802715 is a xanthine derivative available from Hoechst which inhibits both TNF release and TNF action having the following structure:

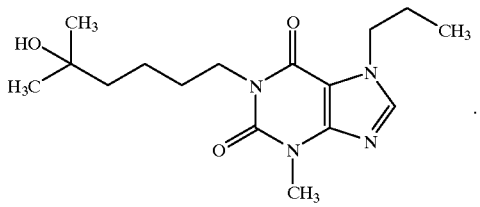

and sulphasalazine.

The histamine antagonists, interleukin-1 antagonists and TNF alpha antagonists may be synthesized or extracted from natural products (plant or animal).

In the compositions according to the invention, the histamine antagonists, interleukin-1 antagonists and/or TNF alpha antagonists are preferably used in an amount ranging from 0.000001 to 5% by weight relative to the total weight of the composition, and especially in an amount ranging from 0.0001 to 0.1% by weight relative to the total weight of the composition.

The compositions according to the invention may be presented in all pharmaceutical dosage forms normally used for topical application, in particular in the form of aqueous, aqueous-alcoholic or oily solutions, of dispersions of the lotion or serum type, of anhydrous or lipophilic gels, of emulsions of liquid or semi-solid consistency of the milk type, obtained by dispersing a fatty phase in an aqueous phase (O/W) or vice versa (W/O), or of suspension or emulsions of soft, semi-solid or solid consistency of the cream or gel type, or alternatively of microemulsions, of microcapsules, of microparticles or of vesicular dispersions of the ionic and/or nonionic type. These compositions are prepared according to standard methods.

They may also be used for the scalp in the form of aqueous, alcoholic or aqueous-alcoholic solutions, or in the form of creams, gels, emulsions or foams or alternatively in the form of aerosol compositions also containing a propellent agent under pressure.

The amounts of the different constituents of the compositions according to the invention are those traditionally used in the fields in question.

These compositions constitute, in particular, cleansing, protective, treatment or skin care creams for the face, hands, feet, major anatomical folds or the body (for example day creams, night creams, make-up removal creams, foundation creams, sun-protection creams), fluid foundations, make-up removal milks, protective or skin care body milks, sun-protection or, better still, after-sun milks, skin care lotions, gels or foams, such as cleansing or disinfecting lotions, sun-protection lotions, artificial tanning lotions, bath compositions, deodorant compositions containing a bactericidal agent, aftershave gels or lotions, depilatory creams, compositions for treating insect bites, pain relief compositions or compositions for treating certain skin disorders such as those mentioned above.

The compositions according to the invention may also consist of solid preparations constituting cleansing bars or soaps.

The compositions may also be packaged in the form of an aerosol composition also containing a propellant agent under pressure.

The histamine antagonists, interleukin-1 antagonists and/or TNF alpha antagonists may also be incorporated in various hair care or treatment compositions, and in particular shampoos, where appropriate antiparasitic, setting lotions, treatment lotions, styling creams or gels, dyeing (normally oxidation dyeing) compositions, where appropriate in the form of colouring shampoos, hair restructuring lotions, permanent-waving compositions (in particular compositions for the first stage of permanent waving), lotions or gels for combating hair loss, and the like.

The compositions of the invention may also be for dentibuccal use, for example a toothpaste or a mouthwash. In this case, the compositions can contain standard adjuvants and additives for compositions for buccal use, and in particular surfactants, thickening agents, humectant agents, polishing agents such as silica, various active ingredients such as fluorides, especially sodium fluoride, and, where appropriate, sweetening agents such as saccharin sodium.

When the composition of the invention is an emulsion, the proportion of the fatty phase can range from 5% to 80% by weight, and preferably from 5% to 50% by weight, relative to the total weight of the composition. The oils, emulsifiers and coemulsifiers used in the composition in emulsion form are chosen from those traditionally used in the cosmetics, pharmaceutical or dermatological fields. The emulsifier and the coemulsifier are present in the composition in a proportion ranging from 0.3% to 30% by weight, and preferably from 0.5 to 30% or, better still, from 0.5 to 20%, by weight relative to the total weight of the composition. The emulsion can, in addition, contain lipid vesicles.

When the composition of the invention is an oily gel or solution, the fatty phase can represent more than 90% of the total weight of the composition.

In a known manner, the composition of the invention may also contain adjuvants which are customary in the cosmetics, pharmaceutical or dermatological field, such as hydrophilic or lipophilic gelling agents, hydrophilic or lipophilic active agents, preservatives, antioxidants, solvents, perfumes, fillers, screening agents, bactericides, odour absorbers and colouring matter. The amounts of these different adjuvants are those traditionally used in the cosmetic, pharmaceutical or dermatological field, and are, for example, from 0.01% to 10% of the total weight of the composition. These adjuvants, depending on their nature, may be introduced into the fatty phase, into the aqueous phase and/or into lipid spherules.

As oils which can be used in the invention, mineral oils (liquid paraffin), vegetable oils (liquid fraction of shea butter, sunflower oil), animal oils (perhydrosqualene), synthetic oils (Purcellin oil), silicone oils (cyclomethicone) and fluorinated oils (perfluoro polyethers) may be mentioned. Fatty alcohols, fatty acids (stearic acid) and waxes (paraffin, carnauba, beeswax) may also be used as fatty substances.

As emulsifiers which can be used in the invention, glyceryl stearate, polysorbate 60 and the PEG-6/PEG-32/glycol stearate mixture sold under the name Tefose® 63 by the company Gattefosse may be mentioned as examples.

As solvents which can be used in the invention, lower alcohols, in particular ethanol and isopropanol, and propylene glycol may be mentioned.

As hydrophilic gelling agents, carboxyvinyl polymers (carbomer), acrylic copolymers such as acrylate/alkylacrylate copolymers, polyacrylamides, polysaccharides such as hydroxypropylcellulose, clays and natural gums may be mentioned, and as lipophilic gelling agents, modified clays such as bentones, metal salts of fatty acids such as aluminium stearates and hydrophobic silica, or alternatively ethylcellulose and polyethylene may be mentioned.

As hydrophilic active agents, proteins or protein hydrolysates, amino acids, polyols, urea, allantoin, sugars and sugar derivatives, water-soluble vitamins, starch and plant extracts, in particular those of Aloe vera may be used.

As lipophilic active agents, retinol (vitamin A) and its derivatives, tocopherol (vitamin E) and its derivatives, essential fatty acids, ceramides and essential oils may be used.

The histamine antagonists, interleukin-1 antagonists and/or TNF alpha antagonists may, inter alia, be combined with active agents intended, in particular, for preventing and/or treating skin complaints. Among these active agents, there may be mentioned, by way of example:

agents which modulate differentiation and/or proliferation and/or skin pigmentation, such as retinoic acid and its isomers, retinol and its esters, vitamin D and its derivatives, oestrogens such as oestradiol, kojic acid or hydroquinone;

antibacterials such as clindamycin phosphate, erythromycin or antibiotics of the tetracyclin class;

antiparasitics, especially metronidazole, crotamiton or pyrethrinoids;

antifungals, especially compounds belonging to the imidazol class such as econazole, ketoconazole or miconazole or their salts, polyene compounds such as amphotericin B, compounds of the allylamine family such as terbinafine, or alternatively octopirox;

steroidal anti-inflammatory agents such as hydrocortisone, betamethasone valerate or clobetasol propionate, or non-steroidal anti-inflammatory agents such as ibuprofen and its salts, diclofenac and its salts, acetylsalicylic acid, acetaminophen or glycyrrhetinic acid;

anaesthetic agents such as lidocaine hydrochloride and its derivatives;

antipruriginous agents such as thenalidine, trimeprazine or cyproheptadine;

antiviral agents such as acyclovir;

keratolytic agents such as alpha- and beta-hydroxycarboxylic or beta-ketocarboxylic acids, their salts, amides or esters, and more especially alpha-hydroxy acids such as glycolic acid, lactic acid, tartaric acid, citric acid and, generally speaking, the fruit acids, and beta-hydroxy acids such as salicylic acid and its derivatives, in particular its alkylated derivatives such as 5-n-octanoylsalicyclic acid;

free-radical scavenging agents such as alpha-tocopherol or its esters, superoxide dismutases, some metal chelators or ascorbic acid and its esters;

antiseborrhoeic agents such as progesterone;

antidandruff agents such as octopirox or pyrithione zinc;

anti-acne agents such as retinoic acid or benzoyl peroxide.

Advantageously, the histamine antagonists, interleukin-1 antagonists and/or TNF alpha antagonists are combined with products having an irritant side-effect, and in particular active agents commonly used in the cosmetics, pharmaceutical or dermatological field. The presence of a histamine antagonist, an interleukin-1 antagonist and/or a TNF alpha antagonist in a cosmetic, pharmaceutical or dermatological composition containing a product or even an active agent having an irritant effect enables this irritant effect to be greatly attenuated or even eliminated.

In particular, the histamine antagonist, interleukin-1 antagonist and/or TNF alpha antagonist make it possible, in particular, to increase the amount of cosmetic, pharmaceutical or dermatological active agent relative to the amount normally used, with a view to improved efficacy.

Thus, the subject of the invention is also a composition containing, in a cosmetically, pharmaceutically or dermatologically acceptable medium, at least one product having an irritant side-effect, characterized in that it contains at least one agent antagonistic to this effect, chosen from interleukin-1 antagonists, TNF alpha antagonists and combinations thereof.

The subject of the invention is also the use, in a topical composition containing a cosmetically, pharmaceutically or dermatologically acceptable medium and at least one product having an irritant side-effect, of at least one compound chosen from histamine antagonists, interleukin-1 antagonists, TNF alpha antagonists and combinations thereof, for eliminating this irritant effect.

The irritant products to which the invention applies are, in particular, perfumes, surfactants (ionic or nonionic), preservatives, some sunscreen agents, organic solvents, alcoholic solutions and some cosmetic, pharmaceutical or dermatological active agents.

In particular, the active agents having an irritant side-effect are chosen from $\alpha$-hydroxy acids (glycolic, lactic, malic, citric, tartaric, mandelic), $\beta$-hydroxy acids (salicylic acid and its derivatives), $\alpha$-keto acids, $\beta$-keto acids, retinoids (retinol and its esters, retinal, retinoic acid and its derivatives, retinoids, in particular those described in the documents RF-A-2,570,377, EP-A-199,636, EP-A-325,540, EP-A-402072), anthralins (dioxyanthranol), anthranoids, peroxides (in particular benzoyl peroxide), minoxidil, lithium salts, antimetabolites, vitamin D and its derivatives, hair dyes or colorants (para-phenylenediamine and its derivatives, aminophenols), alcoholic perfuming solutions (perfumes, toilet water, aftershave, deodorants), antiperspirant agents (some aluminium salts), depilatory or permanent-saving active agents (thiols), depigmenting agents (hydroquinone) and delousing active agents (pyrethrin).

The use of a histamine antagonist, interleukin-1 antagonist and/or TNF alpha antagonist makes it possible, in particular, to multiply from 2- to 10-fold the amount of product, and more especially of active agent, having an irritant side-effect, relative to the prior state of the art, without all the unpleasant sensations mentioned above being experienced. Thus, it is possible to use hydroxy acids up to 50% of the weight of the composition or retinoids up to 5%, without any discomfort.

In particular, the composition contains one or more histamine antagonists, one or more interleukin-1 antagonists and/or one or more TNF alpha antagonists chosen from alkoxy- and/or aryloxytetrazolylbenzofurancarboxamides or an alkoxy- and/or aryloxytetrazolylbenzothiophenecarboxamides and one or more active agents having an irritant side-effect, chosen from alpha-hydroxy acids and beta-hydroxy acids.

The subject of the present invention is, in addition, a cosmetic treatment process, characterized in that a composition as described above, containing at least one TNF alpha antagonist in a cosmetically acceptable medium is applied to the skin, to the scalp and/or to the mucosae.

The cosmetic treatment process of the invention may be carried out, in particular, by applying the hygiene or cosmetic compositions as are defined above according to the customary technique for using these compositions. For example: application of creams, gels, serums, lotions, make-up removal milks or after-sun compositions to the skin or to dry hair, application of a hair lotion to wet hair or of shampoos, or alternatively application of dentifrice to the gums.

The examples which follow illustrate the invention. In these examples, the proportions shown are percentages by weight.

EXAMPLE 1

Make-Up Removal Lotion for the Face

| | |
|---|---|
| Loratidine | 0.05 |
| Antioxidant | 0.05 |
| Isopropanol | 40.00 |
| Preservative | 0.30 |
| Water | qs 100% |

EXAMPLE 2

Make-Up Removal Lotion for the Face

| | |
|---|---|
| Cetirizine | 0.001 |
| Antioxidant | 0.05 |
| Isopropanol | 40.00 |
| Preservative | 0.30 |
| Water | qs 100% |

EXAMPLE 3

Face Care Gel

| | |
|---|---|
| Auranofin | 0.05 |
| Hydroxypropylcellulose (Klucel H sold by the company Hercules) | 1.00 |
| Antioxidant | 0.05 |
| Isopropanol | 40.00 |
| Preservative | 0.30 |
| Water | qs 100 % |

EXAMPLE 4

Face Care Gel

| | |
|---|---|
| Lisophyline | 0.04 |
| Hydroxypropylcellulose (Klucel H sold by the company Hercules) | 1.00 |
| Antioxidant | 0.05 |
| Isopropanol | 40.00 |
| Preservative | 0.30 |
| Water | qs 100 % |

EXAMPLE 5

Face Care Cream (Oil-in-Water Emulsion)

| | |
|---|---|
| Sulphasalazine | 0.02 |
| Glyceryl stearate | 2.00 |
| Polysorbate 60 (Tween 60 sold by the company ICI) | 1.00 |
| Stearic acid | 1.40 |
| Triethanolamine | 0.70 |
| Carbomer | 0.40 |
| Liquid fraction of shea butter | 12.00 |
| Perhydrosqualene | 12.00 |
| Antioxidant | 0.05 |
| Perfume | 0.5 |
| Preservative | 0.30 |
| Water | qs 100% |

EXAMPLE 6

Treatment Shampoo

| | |
|---|---|
| Loratidine | 0.02 |
| Hydroxypropylcellulose (Klucel H sold by the company Hercules) | 1.00 |
| Perfume | 0.50 |
| Preservative | 0.30 |
| Water | qs 100% |

EXAMPLE 7

Antiwrinkle Skin Care Cream for the Face (Oil-in-Water Emulsion)

| | |
|---|---|
| Cetirizine | 0.15 |
| Glyceryl stearate | 2.00 |
| Polysorbate 60 (Tween 60 sold by the company ICI) | 1.00 |
| Stearic acid | 1.40 |
| 5-n-Octanoylsalicylic acid | 0.50 |
| Triethanolamine | 0.70 |
| Carbomer | 0.40 |
| Liquid fraction of shea butter | 12.00 |
| Perhydrosqualene | 12.00 |
| Perfume | 0.50 |
| Preservative | 0.30 |
| Water | qs 100% |

EXAMPLE 8

Emulsified Gel for Treating Insect Bits (Oil-in-Water Emulsion)

| | |
|---|---|
| Cyclomethicone | 3.00 |
| Purcellin oil (sold by the company Dragoco) | 7.00 |
| PEG-6/PEG-32/glycol stearate (Tefose® 63 from Gattefosse) | 0.30 |
| Setastine | 0.02 |

-continued

| | |
|---|---|
| Preservative | 0.30 |
| Perfume | 0.40 |
| Carbomer | 0.60 |
| Crotamiton | 5.00 |
| Glycyrrhetinic acid | 2.00 |
| Ethyl alcohol | 5.00 |
| Triethanolamine | 0.20 |
| Water | qs 100% |

EXAMPLE 9

Pain Relief Gel

| | |
|---|---|
| Cetirizine | 0.03 |
| Hydroxypropylcellulose (Klucel H sold by the company Hercules) | 1.00 |
| Antioxidant | 0.05 |
| Lidocaine hydrochloride | 2.00 |
| Isopropanol | 40.00 |
| Preservative | 0.30 |
| Water | qs 100% |

EXAMPLE 10

Cream for Treating Solar Erythema (Oil-in-Water Emulsion)

| | |
|---|---|
| Dexchlorpheniramine | 0.25 |
| Glyceryl stearate | 2.00 |
| Polysorbate 60 (Tween 60 sold by the company ICI) | 1.00 |
| Stearic acid | 1.00 |
| Glycyrrhetinic acid | 2.00 |
| Triethanoiamine | 0.70 |
| Carbomer | 0.40 |
| Liquid fraction of shea butter | 12.00 |
| Sunflower oil | 10.00 |
| Antioxidant | 0.05 |
| Perfume | 0.5 |
| Preservative | 0.30 |
| Water | qs 100% |

EXAMPLE 11

Antiwrinkle Skin Care Cream for the Face (Oil-in-Water Emulsion)

This example differs from Example 7 by the replacement of cetirizine by 3-benzyloxy-5-methoxy-N-(1H-tetrazol-5-yl)benzothiophene-2-carboxamide, manufactured according to Example 1 of the document EP-A-299,457, and 5-n-octanoylsalicylic acid by glycolic acid.

EXAMPLE 12

Antiwrinkle Skin Care Cream for the Face (Oil-in-Water Emulsion)

This example differs from Example 7 by the replacement of sulphasalazine by 5-methoxy-3-phenoxy-N-(1H-tetrazol-5-yl)benzothiophene-2-carboxamide, manufactured according to Example 2 of the document EP-A-299,457, and 5-n-octanoylsalicylic acid by a fruit acid mixture (lactic, glycolic, tartaric, citric and malic acids).

EXAMPLE 13

Gel for Treating Acne

| | |
|---|---|
| all-trans-Retinoic acid | 0.05 |
| Loratidine | 0.55 |
| Hydroxypropylcellulose (Klucel H sold by the company Hercules) | 1 |
| Antioxidant | 0.05 |
| Isopropanol | 40 |
| Preservative | 0.3 |
| Water | qs 100 % |

We claim:

1. A method for treatment of sensitive skin to treat one of the following symptoms (i) sores and/or erythema; (ii) dysesthetic sensations; (iii) sensations of inflammation; (iv) pruritus; (v) prickling; (vi) tingling; (vii) discomfort; and (viii) tightness of the skin, and/or mucosae, comprising administering a composition adopted for treatment of sensitive skin which comprises a cosmetically, dermatologically or pharmaceutically effective amount of at least one compound selected from the group consisting of interleukin-1 antagonists, TNF alpha antagonists and combinations thereof which is contained in a cosmetically, dermatologically or pharmaceutically acceptable medium, wherein said interleukin-1 antagonist is selected from the group consisting of auranofin, SKF-105809, and lactoferrin, and said TNF-alpha antagonist is selected from the group consisting of lisophyline, A802715 and sulphasalzine.

2. The method of claim 1, wherein the composition administered further comprises at least one histamine antagonist selected from the group consisting of cinnarizine, cyclizine, dexchlorpheniramine, triprolidine, promethazine, alimemazine, cetirizine hydrochloride, ebastine, loratadine, selastine hydrochloride, 5methoxy-3-phenoxy-N-(1H-tetrazol-5-yl)benzothiophene-2-carbox-amide,5-methoxy-3-(1-methylethoxy)-N-(1H-tetrazol-5-yl)benzothiophene-2-carbox-amide,6-methoxy-3-(1methylethoxy)-N-(1H-tetrazol-5-yl)benzothiophene-2-carbox-amide, 5-methoxy-3-(1-methylethyl)-N-(1H-tetrazol-5-yl)benzothiophene-2-carbox-amide. 3-benzyloxy-5-methoxy-N-(1H-tetrazol-5-yl)benzothiophene-2-carboxamide, and 5-methoxy-3-phenoxy-N-(1H-tetrazol-5-yl)benzothiophene-2-carboxamide.

3. The method of claim 1, wherein the amount of the compound contained in the composition ranges from about 0.000001 to 5% by weight relative to the total weight of the composition.

4. The method of claim 1, wherein the amount of the compound contained in the composition ranges from about 0.0001 to 0.1% by weight relative to the total weight of the composition.

5. The method of claim 1, wherein the cosmetically, pharmaceutically, or dermatologically acceptable medium comprises an aqueous, oil or aqueous alcoholic solution, a water-in-oil emulsion, an oil-in-water emulsion, a microemulsion, an aqueous gel, an anhydrous gel, a serum, or a dispersion of vesicles, microcapsules or microparticles.

6. The method of claim 1, wherein the composition further contains at least one agent selected from the group consisting of anti-bacterial, antiparasitic, antifungal, anti-inflammatory, antipruriginous, anaesthetic, antiviral, keratolytic, free-radical scavenging antiseborrhoeic, anti-dandruff and anti-acne agents and agents which modulate the differentiation or the proliferation or the pigmentation of skin.

7. The method according to claim 6, wherein the agent is selected from the group consisting of lidocaine hydrochloride, antiparasitic agents and non-steroidal anti-inflammatory agents.

8. A method of treating irritable skin to alleviate a symptom selected from the group consisting of (i) sores and/or erythema; (ii) dysesthetic sensations; (iii) sensations of inflammation; (iv) pruritus; (v) prickling; (vi) tingling; (vii) discomfort; and (viii) tightness of the skin, and/or mucosae, comprising topically administering a composition adopted for treatment of irritable skin comprising an effective amount of at least one compound selected from the group consisting of interleukin-1 antagonists, TNF alpha antagonists and combinations thereof, wherein said interleukin-1 antagonists is selected from the group consisting of auranofin, SKF-105809, and lactoferrin, and said TNF-alpha antagonist is selected from the group consisting of lisophyline, A802715 and sulphasalzine.

9. The method of claim 8, wherein the topically administered composition additionally comprises at least one histamine antagonist selected from the group consisting of cinnarizine, cyclizine, dexchlorpheniramine, triprolidine, promethazine, alimemazine, cetirizine hydrochloride, ebastine, loratadine, selastine hydrochloride, 5-methoxy-3-phenoxy-N-(1H-tetrazol-5-yl)benzothiophene-2-carboxamide, 5-methoxy-3-(1-methylethoxy)-N-(1H-tetrazol-5-yl)benzothiophene-2-carboxamide, 6-methoxy-3-(1-methylethoxy)-N-(1H-tetrazol-5-yl)benzothiophene-2-carboxamide, 5-methoxy-3-(1-methylethyl)-N-(1H-tetrazol-5-yl)benzothiophene-2-carboxamide, 3-benzyloxy-5-methoxy-N-(1H-tetrazol-5-yl)benzothiophene-2-carboxamide, and 5-methoxy-3-phenoxy-N-(1H-tetrazol-5-yl)benzothiophene-2-carboxamide.

10. A method of treating irritable skin to alleviate a symptom selected from the group consisting of (i) sores and/or erythema; (ii) dysesthetic sensations; (iii) sensations of inflammation; (iv) pruritus; (v) prickling; (vi) tingling; (vii) discomfort; and (viii) tightness of the skin, and/or mucosae, comprising topically administering a composition adopted for topical treatment of irritable skin comprising an effective amount of at least one histamine antagonist selected from the group consisting of cinnarizine, cyclizine, dexchlorpheniramine, triprolidine, promethazine, alimemazine, cetirizine hydrochloride, ebastine, loratadine, selastine hydrochloride, 5-methoxy-3-phenoxy-N-(1H-tetrazol-5-yl)benzothiophene-2-carboxamide, 5-methoxy-3-(1-methylethoxy)-N-(1H-tetrazol-5-yl)benzothiophene-2-carboxamide, 6-methoxy-3-(1-methylethoxy)-N-(1H-tetrazol-5-yl)benzothiophene-2-carboxamide, 5-methoxy-3-(1-methylethyl)-N-(1H-tetrazol-5-yl)benzothiophene-2-carboxamide, 3-benzyloxy-5-methoxy-N-(1H-tetrazol-5-yl)benzothiophene-2-carboxamide, and 5-methoxy-3-phenoxy-N-(1H-tetrazol-5-yl)benzothiophene-2-carboxamide.

11. The method of claim 8, wherein the amount of the compound contained in the composition ranges from about 0.000001 to 5% by weight relative to the total weight of the composition.

12. The method of claim 9, wherein the amount of the histamine antagonist contained in the composition ranges from about 0.000001 to 5% by weight relative to the total weight of the composition.

13. The method of claim 10, wherein the amount of the histamine antagonist contained in the composition ranges from about 0.00001 to 5% by weight relative to the total weight of the composition.

14. The method of claim 8, wherein the amount of the compound contained in the composition ranges from about 0.0001 to 0.1% by weight relative to the total weight of the composition.

15. The method of claim 9, wherein the amount of the histamine antagonist contained in the composition ranges from about 0.0001 to 0.1% by weight relative to the total weight of the composition.

16. The method of claim 10, wherein the amount of the histamine antagonist contained in the composition ranges from about 0.0001 to 0.1% by weight relative to the total weight of the composition.

17. A method of cosmetic treatment comprising topically applying to the skin, scalp and/or the mucosae a topically administrable composition containing at least one TNF alpha-antagonist compound contained in a cosmetically acceptable medium, wherein said at least one TNF alpha antagonist compound is selected from the group consisting of lisophyline, A802715 and sulphasalzine.

18. The method of claim 17, wherein the amount of the compound contained in the composition ranges from about 0.000001 to 5% by weight relative to the total weight of the composition.

19. The method of claim 17, wherein the amount of the compound contained in the composition ranges from about 0.0001 to 0.1% by weight relative to the total weight of the composition.

20. A method of claim 1, wherein said composition further comprises at least one irritant active agent selected from the group consisting of an alpha-hydroxy acid, beta-hydroxy acid, alpha-keto acid, beta-keto acid, retinoid, an anthralin, an anthranoid, benzoyl peroxide, minoxidil, a lithium salt, an anti-metabolite, vitamin D, a hair dye or colorant, an alcoholic perfuming solution, an antiperspirant agent, a depilatory agent, a permanent waving agent, a depigmenting agent, and a delousing active agent.

* * * * *

UNITED STATES PATENT AND TRADEMARK OFFICE
CERTIFICATE OF CORRECTION

PATENT NO.   : 5,993,833
DATED        : November 30, 1999
INVENTOR(S)  : De Lacharriere et al It is certified that error appears in the above-identified patent and that said Letters Patent is hereby corrected as shown below:

IN THE ABSTRACT:
Title page,
Line 7 of the Abstract, delete "dysaesthetic" and replace with --dysaesthesic--;

Column 1
Line 47, delete "dysaesthetic" and replace with --dysaesthesic--;
Line 48, delete "Dysaesthetic" and replace with --Dysaesthesic--;

Column 2
Line 25, delete "aesthetic" and replace with --aesthesic--;

Column 3
Line 20, delete "dysaesthetic" and replace with --dysaesthesic--;
Line 25, delete "dysaesthetic" and replace with --dysaesthesic--;
Line 42, delete "dysaesthetic" and replace with --dysaesthesic--;

Column 12
Line 26, delete "dysaesthetic" and replace with --dysaesthesic--;

UNITED STATES PATENT AND TRADEMARK OFFICE
CERTIFICATE OF CORRECTION

PATENT NO.    : 5,993,833
DATED         : November 30, 1999
INVENTOR(S)   : De Lacharriere et al It is certified that error appears in the above-identified patent and that said Letters Patent is hereby corrected as shown below:

<u>Column 13</u>
Line 5, delete "dysaesthetic" and replace with --dysaesthesic--;
Line 34, delete "dysaesthetic" and replace with --dysaesthesic--.

Signed and Sealed this

Third Day of July, 2001

Attest:

*Attesting Officer*

NICHOLAS P. GODICI
*Acting Director of the United States Patent and Trademark Office*